US00PP18281P3

(12) United States Plant Patent
Randag

(10) Patent No.: US PP18,281 P3
(45) Date of Patent: Dec. 4, 2007

(54) **VARIETY OF *CALLA* LILLY NAMED 'VERMEER'**

(50) Latin Name: *Zantedeschia sprengeri*
Varietal Denomination: Vermeer

(75) Inventor: Cecilius Jan-Jochem Randag, CJ 't Zand (NL)

(73) Assignee: Sande BV, CJ't Zand (NL)

( * ) Notice: Subject to any disclaimer, the term of this patent is extended or adjusted under 35 U.S.C. 154(b) by 82 days.

(21) Appl. No.: 11/348,986

(22) Filed: Feb. 7, 2006

(65) Prior Publication Data

US 2007/0186323 P1 Aug. 9, 2007

(51) Int. Cl.
*A01H 5/00* (2006.01)

(52) U.S. Cl. ..... Plt./263

(58) Field of Classification Search ..... Plt./263
See application file for complete search history.

(56) References Cited

U.S. PATENT DOCUMENTS

PP15,282 P2 * 10/2004 Randag ..... Plt./263

* cited by examiner

*Primary Examiner*—Wendy C Haas
(74) *Attorney, Agent, or Firm*—The Webb Law Firm

(57) ABSTRACT

'Vermeer' is a new variety of *calla* lily having a flower with a white and purple colored spathe producing 1–15 flowers per tuber. The flower stems are about 60 cm in height. The leaves are green with whitish spots and have a leathery texture.

3 Drawing Sheets

Botanical classification: *Zantedeschia sprengeri*.
Varietal denomination: 'Vermeer'.

BACKGROUND OF THE INVENTION

The present invention comprises a new and distinct cultivar of *calla* lily, botanically known as *Zantedeschia sprengeri* and hereinafter referred to by the cultivar name 'Vermeer'.

'Vermeer' is the result of a planned breeding program which had the objective of creating *Zantedeschia* hybrids for cut flower production in a wide range of colors with a large, classic flower shape. The breeding program began in 1989 and the new cultivar is a seedling selected from the crossing of *Zantedeschia sprengeri* seedling 95845 (female parent) with *Zantedeschia sprengeri* seedling 95846 (male parent). 'Vermeer' was selected in 2001 by the inventor C. J. J. Randag in 't Zand, The Netherlands, as one flowering plant within the progeny of the stated cross.

The first act of asexual reproduction of 'Vermeer' by tissue culture was performed by the inventor in August of 2001 in 't Zand, The Netherlands. Subsequent asexual reproduction by tissue culture at the same location has demonstrated that the combination of characteristics as herein disclosed for the new cultivar are retained through successive generations of asexual reproduction.

The following observations, measurements and comparisons describe plants grown in 't Zand, The Netherlands under greenhouse conditions which approximate those generally used in horticultural practice. Color references are made to the R.H.S. Colour Chart of The Royal Horticulture Society of London, except where general color terms of ordinary significance are used.

The present variety has not been evaluated under all possible environmental conditions. The phenotype may vary with variations in environment without a change in the genotype of the plant.

The following traits have been repeatedly observed and determined to basic characteristics of 'Vermeer' which, in combination, distinguish this *calla* lily as a new and distinct cultivar:

1. Round, white and purple spathe;
2. Fast forcing time; and
3. High flower production.

Table 1 provides similarities and differences of 'Vermeer' to its parents and *Zantedeschia sprengeri* variety 'Picasso' U.S. Plant Pat. No. PP15,282.

TABLE 1

| 'Vermeer' | Similarities | Differences |
|---|---|---|
| 95845 (female parent) | leaf shape | Spathe color |
| 95846 (male parent) | leaf shape | Spathe color<br>Spathe shape |
| 'Picasso' (PP15,282) | leaf shape | Spathe colour<br>Spathe shape<br>Number of white spots on leaves |

BRIEF DESCRIPTION OF THE DRAWINGS

The accompanying photographic drawings illustrate the new variety, with the colors being as nearly true as is possible with color illustrations of this type.

DESCRIPTION OF THE PLANT

Figure 1:
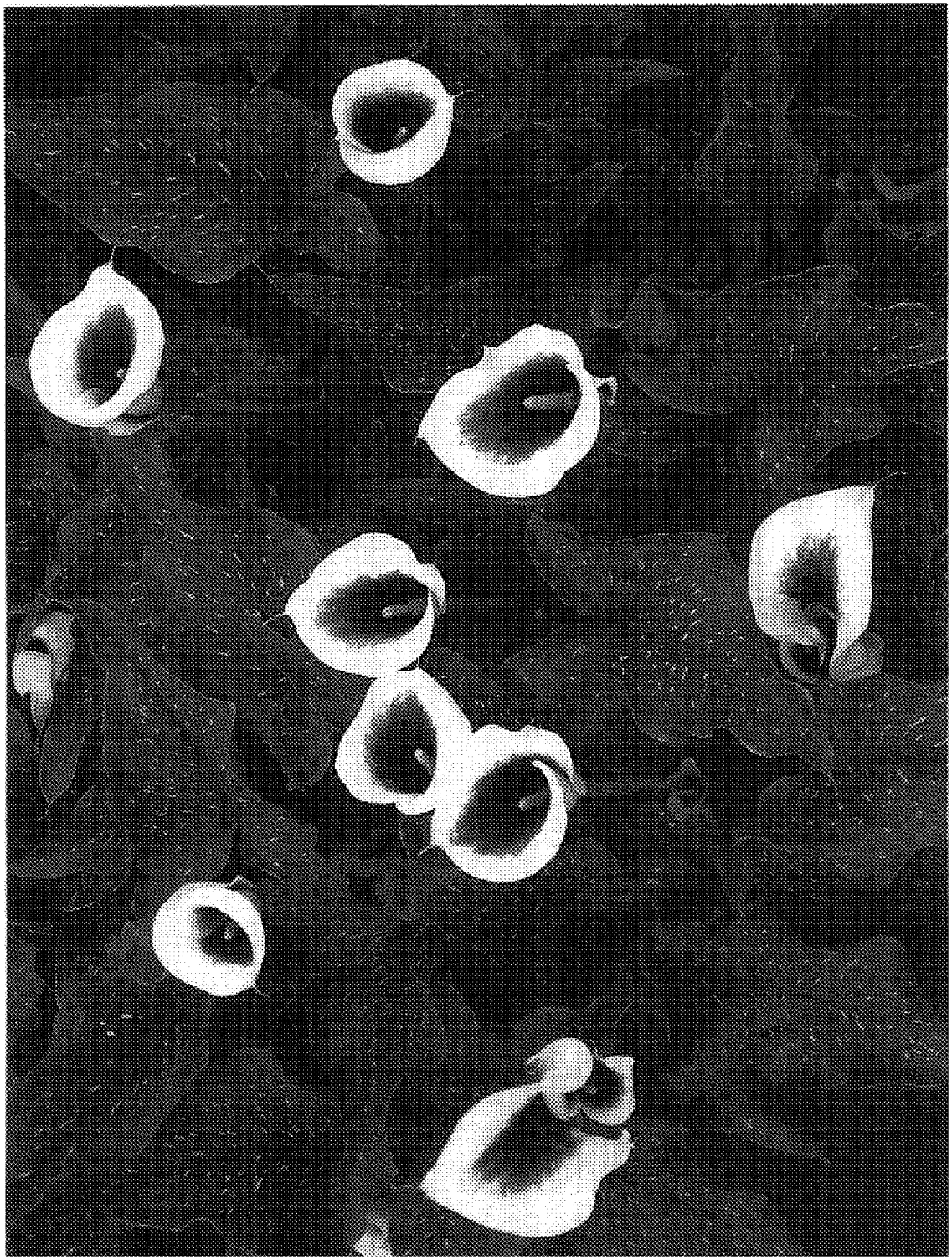
FIG. 1 is a photograph of the flowers and leaves of the new variety.
Figure 2:
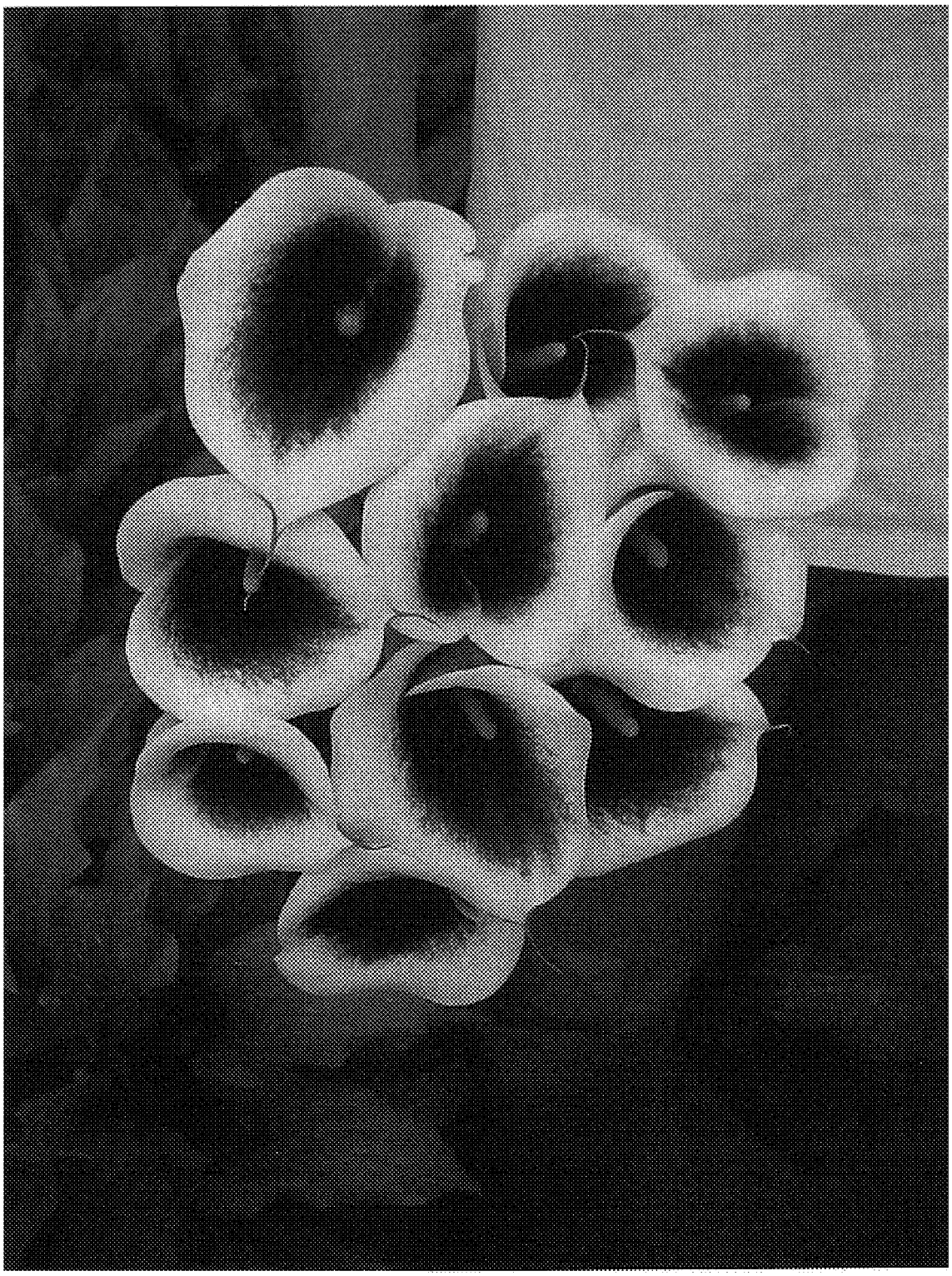
FIG. 2 is a close-up photograph of flowers of the new variety.
Figure 3:
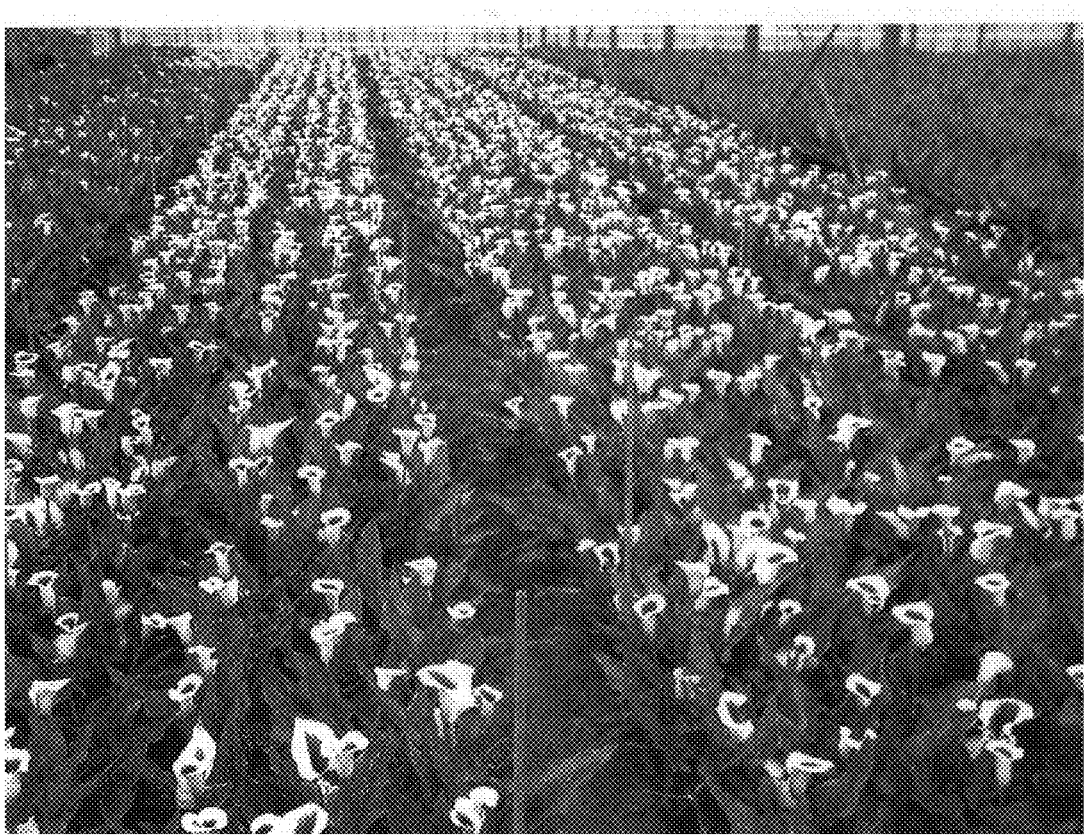
FIG. 3 is a photograph that illustrates the stability of the crop after tissue culture.

Size:

*Height of the leaf canopy above the soil.*—45–70 cm.

*Height of top of lower above the soil.*—70–100 cm.

*Diameter.*—30–45 cm.

Form: Erect.

Number of flowers per tuber:

*Size* 9–12 *cm in diameter.*—1–2 flowers.

*Size* 12–15 *cm in diameter.*—3–4 flowers.

*Size* 15–18 *cm in diameter.*—5–8 flowers.

Branches:

*Character.*—Many, like the variety 'Celeste'.

*Average number.*—5.

*Color.*—Between Green Group 143A and Yellow-Green Group 144B with spots of Red Group 46A.

*Length.*—45–50 cm.

*Diameter.*—15–20 cm.

Leaves:

*Size.*—Width: 10–15 cm. Length: 20–35 cm.

*Number per plant.*—7–25.

*Shape.*—Sagittate.

*Color.*—Upper surface: Green Group 136A to 137A. Lower surface: Green Group 136A to 137A.

*Margin.*—Wavy.

*Veins.*—Configuration: Pinnate. Color: Yellow-Green Group 147A.

*Surface quantity.*—Leathery.

*Petiole.*—Length: 35–60 cm. Color: The base is between Yellow-Green Group 144A and 145A with Red-Group 46A spots. The upper part of the petiole is between Yellow-Green Group 144A and 145A.

Roots:

*Color.*—White.

*Branching.*—Not different from other *Zantedeschia.*

THE FLOWER

Spathe:

*Size.*—Length: 5–9 cm. Width: 5–8 cm.

*Color.*—Upper surface: The base is Green-White Group 157A with a second color of purple between Purple Group 76A and 76C. Lower surface: The base color is Green-White Group 157A with a second color of purple between Purple Group 76A and 76C.

*Vein color.*—Varies between Black Group 202C and 202D.

*Shape.*—Round.

Spadix:

*Size.*—Length: 15–40 mm. Diameter: 5–7 mm.

*Color.*—Between Yellow-Orange Group 16B and 16C.

*Position relative to spathe.*—Upright.

Peduncle:

*Size.*—Length: 50–80 cm. Diameter: 8–12 mm.

*Color.*—Varies between Yellow-Green Group 144C and 145A.

Reproductive organs:

*Location of female organs.*—Basal position of the spadix.

*Location of male organs.*—Upper position of the spadix.

*Perianth.*—Conspicuous.

*Stamens.*—Not visible before pollen release.

Pistil:

*Length.*—About 1 mm.

GENERAL

Disease resistance: No unusual susceptibility to diseases noticed to date.

Pest resistance: No unusual susceptibility to pests noticed to date.

Heat tolerance: No heat tolerance.

Hardiness: Not hardy.

Flowering: Tubers planted in a greenhouse in The Netherlands in February produce flowers in April. Tubers planted outdoors in The Netherlands in May produce flowers in July.

Lastingness: About two weeks on the plant.

Fragrance: None.

I claim:

1. A new and distinct variety of *calla* lily plant named 'Vermeer' as herein described and illustrated.

* * * * *